US008483796B2

(12) United States Patent
Nahm

(10) Patent No.: US 8,483,796 B2
(45) Date of Patent: Jul. 9, 2013

(54) ARRANGEMENT AND METHOD FOR QUANTITATIVELY DETERMINING THE BLOOD FLOW WITHIN BLOOD VESSELS

(75) Inventor: Werner Nahm, Buehlerzell (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 13/335,559

(22) Filed: Dec. 22, 2011

(65) Prior Publication Data

US 2012/0190967 A1 Jul. 26, 2012

(30) Foreign Application Priority Data

Dec. 23, 2010 (DE) .......................... 10 2010 055 772

(51) Int. Cl.
*A61B 5/05* (2006.01)
(52) U.S. Cl.
USPC ............ 600/411; 600/419; 600/427; 600/476
(58) Field of Classification Search
USPC .................. 600/411, 419, 427, 468, 454, 465
See application file for complete search history.

(56) References Cited

U.S. PATENT DOCUMENTS

| 3,778,614 | A | 12/1973 | Hounsfield |
| 4,399,509 | A | 8/1983 | Hounsfield |
| 4,707,658 | A | 11/1987 | Frahm et al. |
| 6,373,920 | B1 | 4/2002 | Hsieh |
| 6,546,275 | B2 * | 4/2003 | Carroll .......................... 600/419 |
| 7,580,185 | B2 | 8/2009 | Haisch et al. |
| 2008/0013166 | A1 | 1/2008 | Haisch et al. |
| 2008/0097194 | A1 * | 4/2008 | Milner ............................ 600/425 |
| 2008/0119720 | A1 * | 5/2008 | Carroll et al. .................. 600/410 |
| 2008/0234586 | A1 | 9/2008 | Tearney et al. |
| 2009/0030321 | A1 * | 1/2009 | Baba et al. ..................... 600/454 |
| 2010/0061610 | A1 | 3/2010 | Van De Haar |
| 2010/0097618 | A1 | 4/2010 | Haisch et al. |
| 2010/0113900 | A1 | 5/2010 | Shakespeare et al. |

(Continued)

FOREIGN PATENT DOCUMENTS

| DE | 103 39 784 A1 | 3/2004 |
| EP | 0 244 596 A1 | 11/1987 |
| WO | WO2009/008745 A2 | 1/2009 |

OTHER PUBLICATIONS

"Hightech-Einsatz bei erkrankten Hirngefaessen", www.innovations-report/de/html/berichte/medizin_gesundheit/bericht-25207.html dated Jan. 28, 2004, pp. 1 to 3, on the internet.

(Continued)

*Primary Examiner* — Jonathan Cwern
*Assistant Examiner* — Shahdeep Mohammed
(74) *Attorney, Agent, or Firm* — Walter Ottesen, P.A.

(57) ABSTRACT

An arrangement quantitatively determines the blood flow within blood vessels through which blood flows in a volume of a tissue defining a surface. Three-dimensional first image data of a first volume portion of the volume is detected and optical second image data is detected continuously in time of a first surface portion of the surface. A calibrating unit of the arrangement calibrates the relative value of the flow speed and/or the volumetric flow of the blood flowing through the blood vessels disposed directly below the first surface portion based on the absolute values of the flow speed and/or of the volumetric flow of the blood. An output unit outputs the absolute values of the flow speed and/or the volumetric flow of the blood flowing through the blood vessels arranged directly below the first surface portion.

15 Claims, 8 Drawing Sheets

Legend
102 – calculation module
103 – servomotor-control calculation module
104 – additional calculation module
105 – additional calculation module
112 – calculation module
113 – matching module
114 – calibration module
115 – absolute value calculator
120 – servomotor control
121 – inductive flow sensor
122 – additional calculation module

U.S. PATENT DOCUMENTS

| | | |
|---|---|---|
| 2010/0280398 A1 | 11/2010 | Hachiga et al. |
| 2011/0013002 A1 | 1/2011 | Thompson et al. |
| 2011/0137177 A1* | 6/2011 | Toma et al. ............... 600/473 |
| 2011/0168914 A1 | 7/2011 | Haisch et al. |

OTHER PUBLICATIONS

"NOVA Overview", www.vassolinc.com/product.cfm, p. 1, copyright 2004-2011, on the internet.

Paul, P. et al, "A surface registration approach for video-based analysis of intraoperative brain surface deformations", HAL author manuscript, Workshop on Augmented Environments for Medical Imaging and Computer-Aided S, inserm-00109455, version 1, MICCAI, 2006.

NOVA report, "Volumetric Flow Rate", created Oct. 20, 2004.

English translation of German office action dated Dec. 13, 2011 in the corresponding German application.

\* cited by examiner

Legend
102 – calculation module
103 – servomotor-control calculation module
104 – additional calculation module
105 – additional calculation module
112 – calculation module
113 – matching module
114 – calibration module
115 – absolute value calculator
120 – servomotor control
121 – inductive flow sensor
122 – additional calculation module

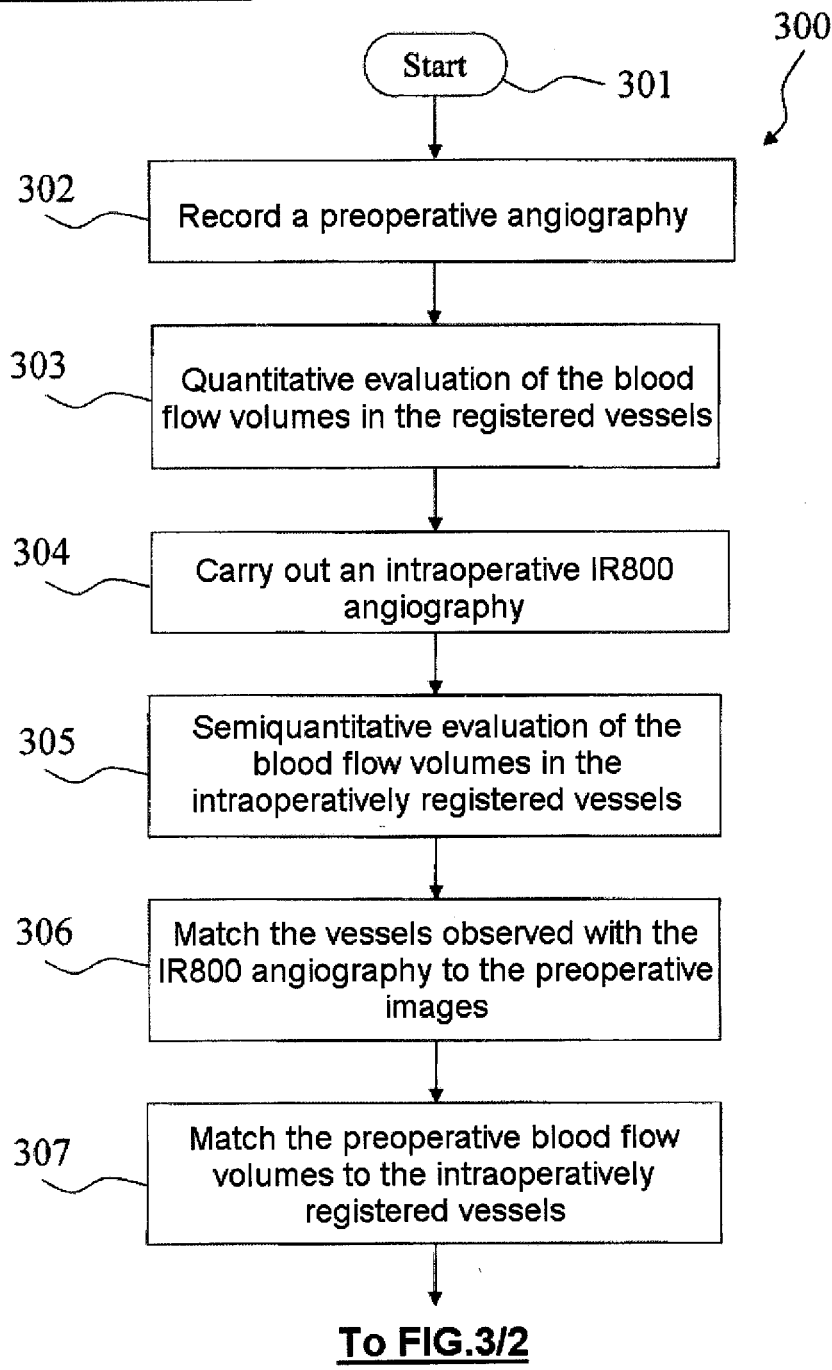

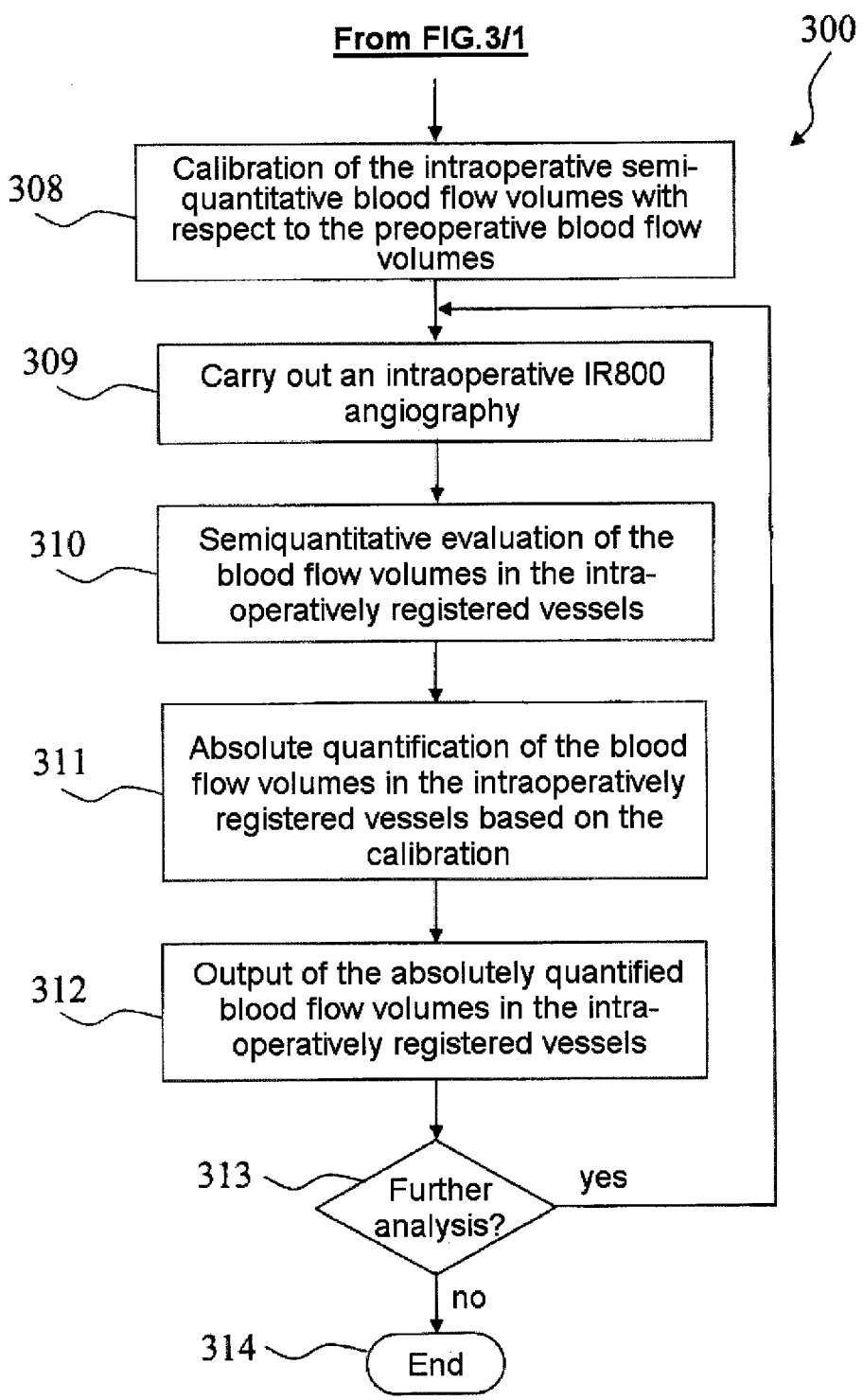

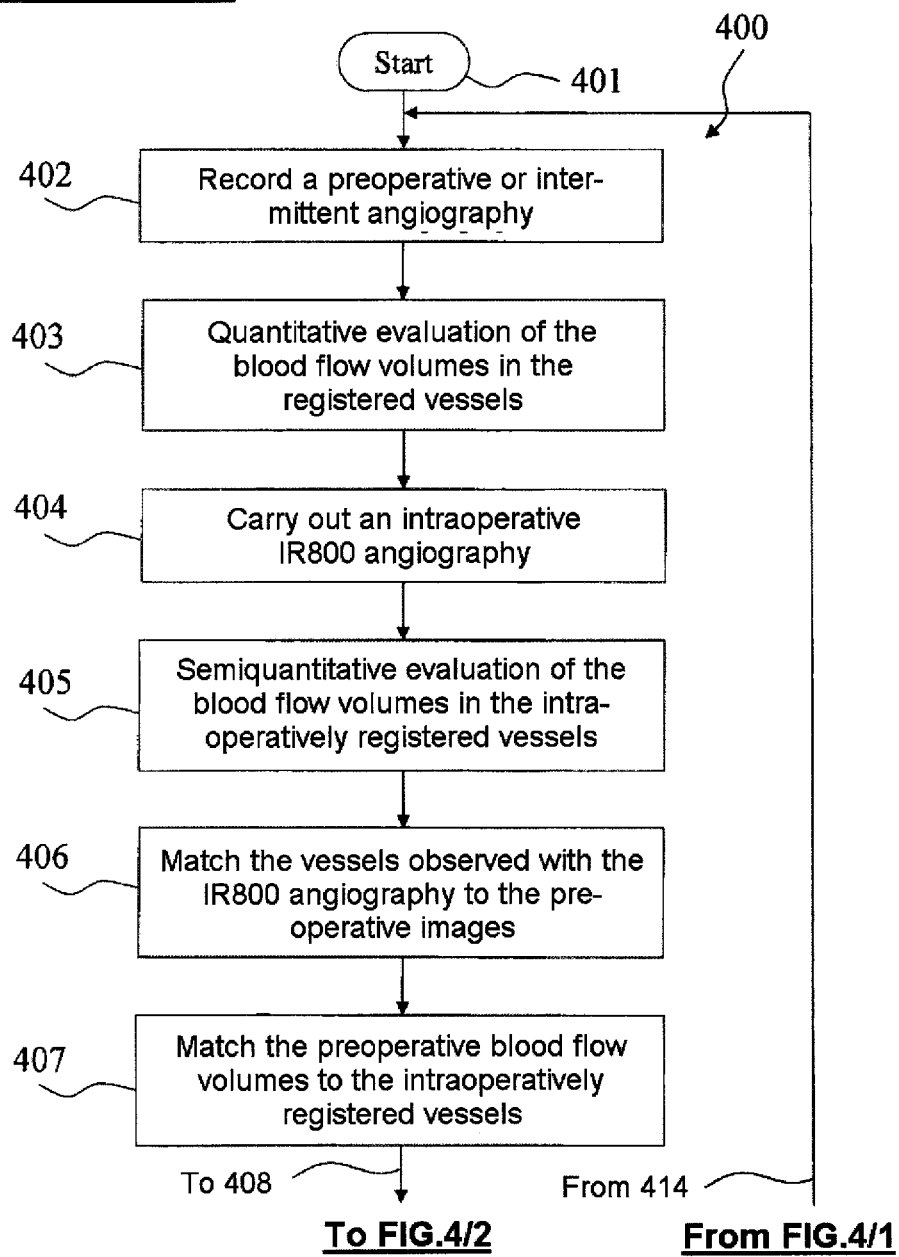

FIG.4 / 2
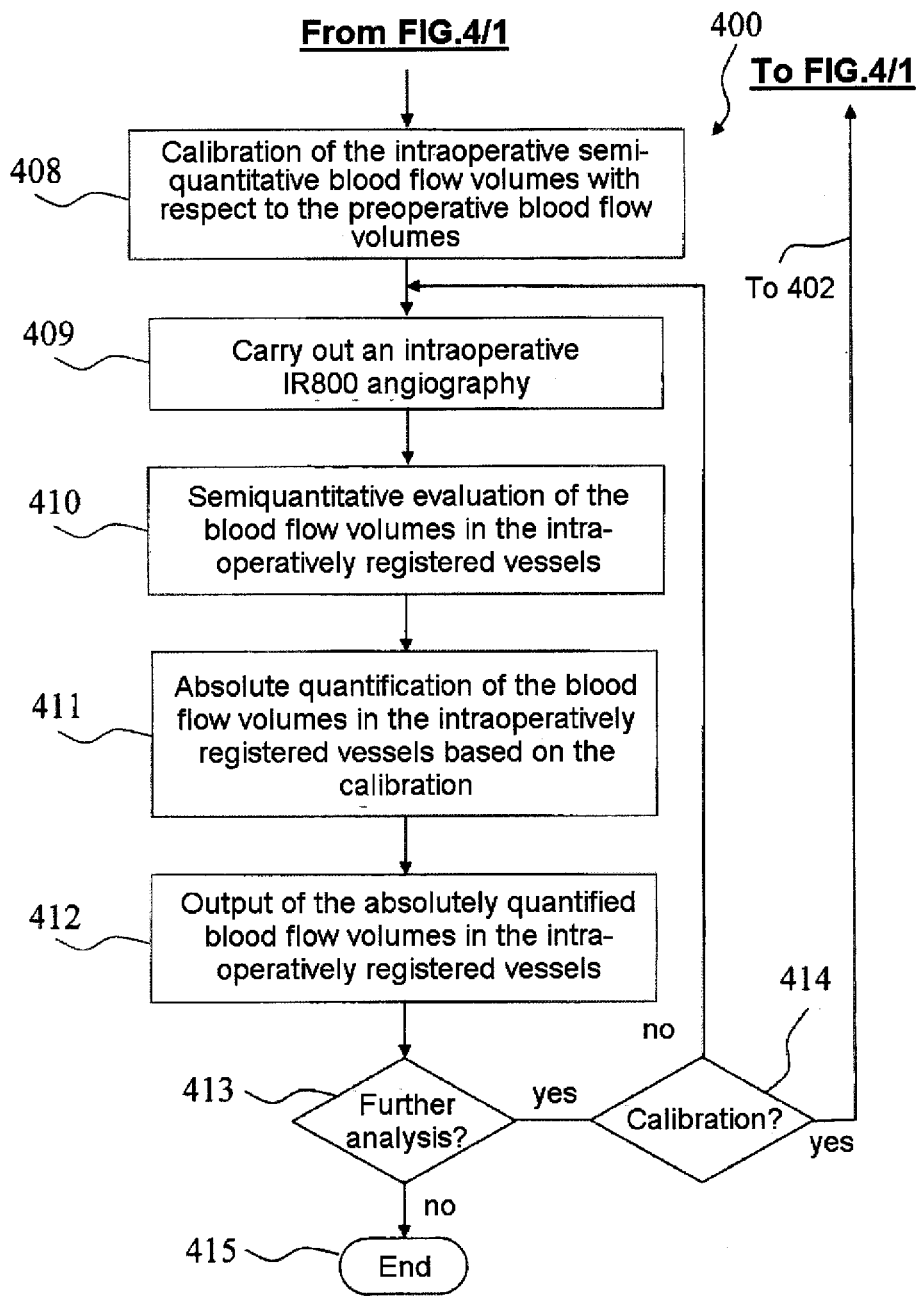

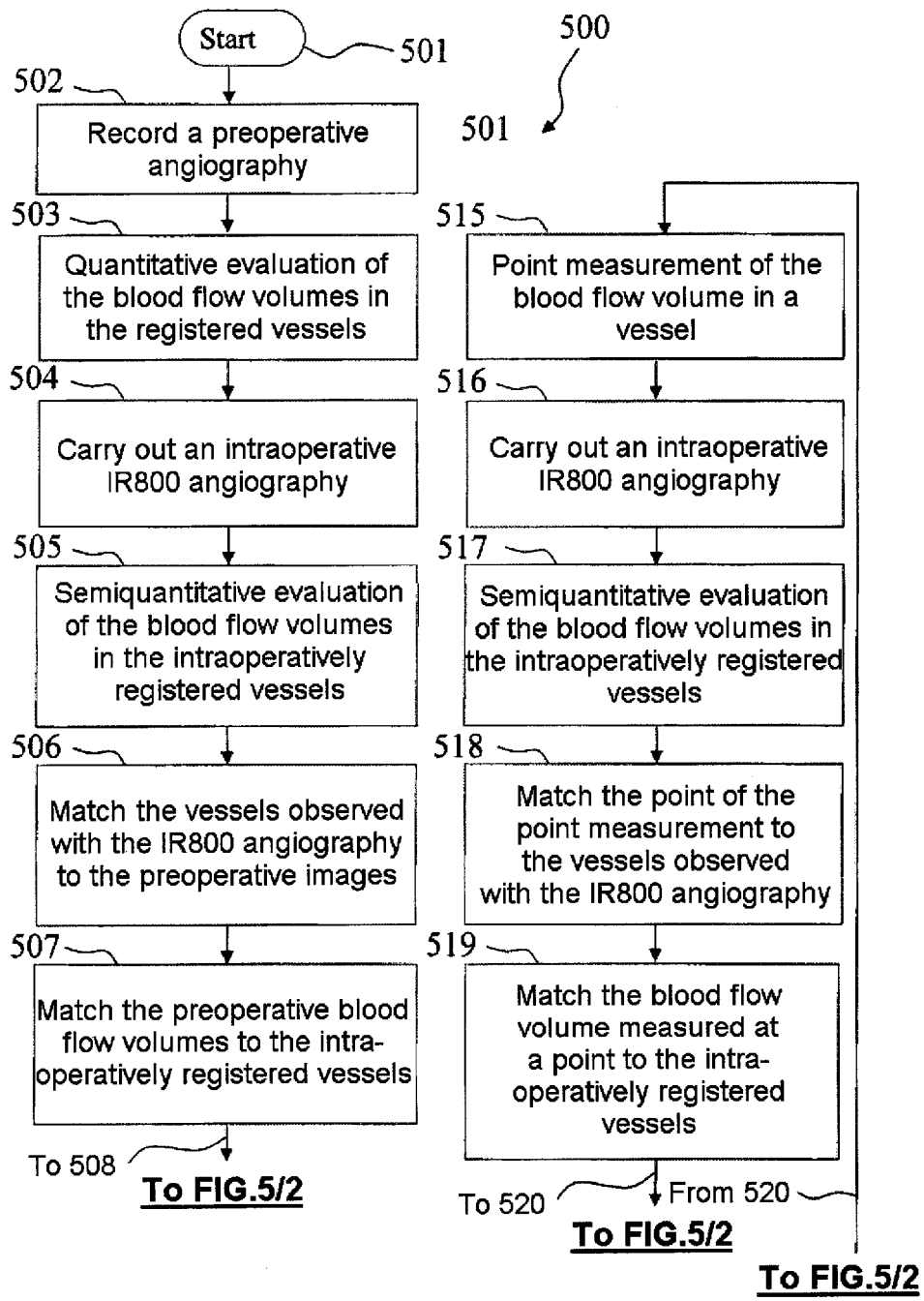

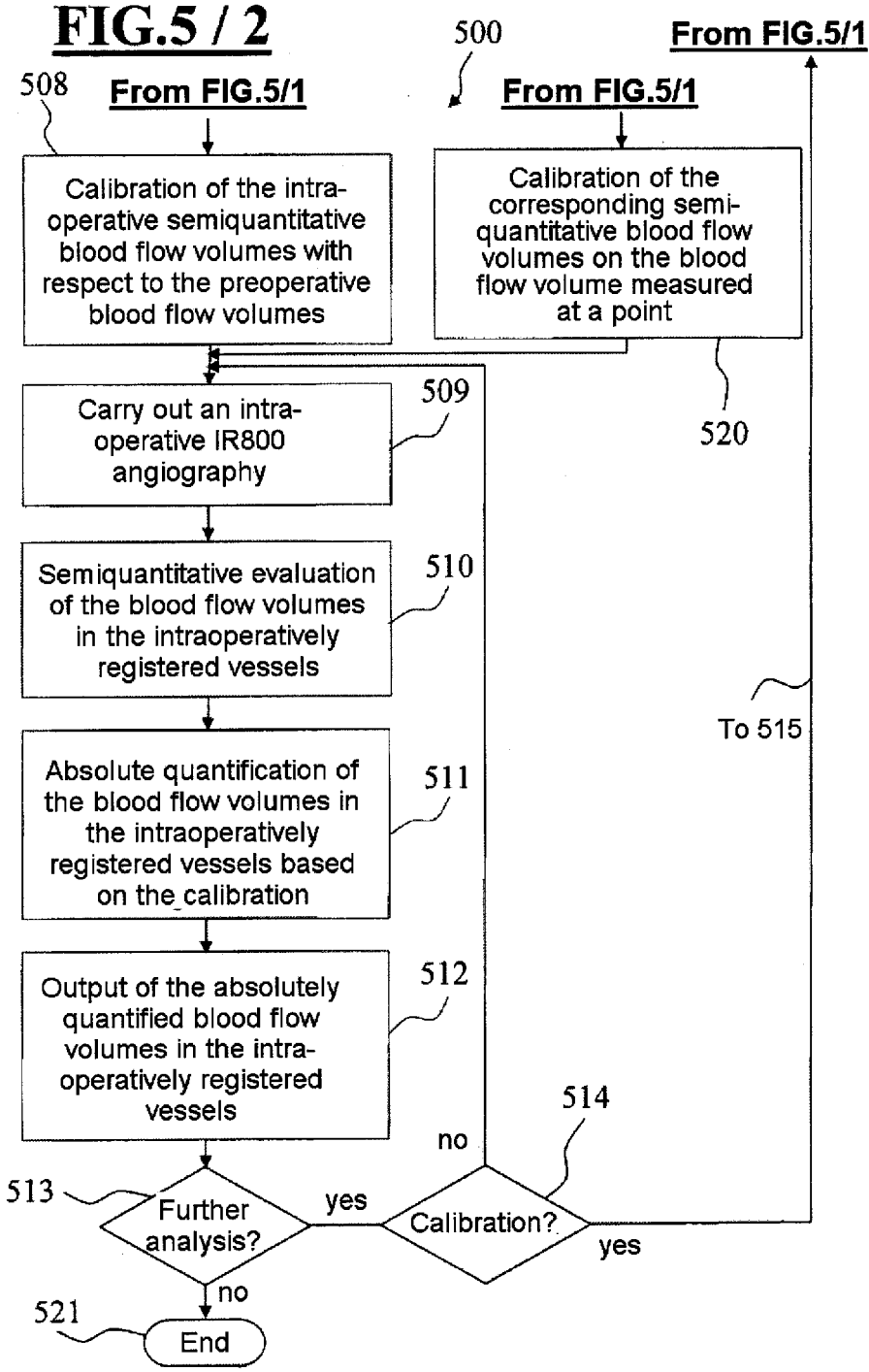

ARRANGEMENT AND METHOD FOR QUANTITATIVELY DETERMINING THE BLOOD FLOW WITHIN BLOOD VESSELS

CROSS REFERENCE TO RELATED APPLICATION

This application claims priority of German patent application no. 10 2010 055 772.2, filed Dec. 23, 2010, the entire content of which is incorporated herein by reference.

FIELD OF THE INVENTION

The invention relates to an arrangement for quantitatively determining the blood flow within blood vessels and to a method for quantitatively determining the blood flow within blood vessels.

BACKGROUND OF THE INVENTION

In medicine, the display of vessels, usually blood vessels, by means of diagnostic imaging methods is called angiography. To this end, a contrast agent, that is, a substance that increases the image contrast or makes it particularly visible in the selected examination method, is often injected into the vessel. The vessel interior filled with the contrast agent then stands out in the image of the recorded body region. The resulting image is called an angiogram.

A distinction is made between different angiographies, depending on the underlying medical imaging method.

In the case of optical angiography, a video recording is generally made of the optical dye front, which is passing through, of an optically detectable contrast agent which was injected in the form of a bolus into the vessel to be examined. It can only measure changes in the blood flow that are close to the surface. A special case of optical angiography is the so-called fluorescence angiography, in which there is photographic representation of the blood vessels with the aid of fluorescent dyes. U.S. Pat. No. 7,580,185 and U.S. patent application publications 2008/0013166, 2010/0097618 and 2011/0168914 describe such a video fluorescence angiography method and a microscope system for carrying out the method. A corresponding system is marketed by Carl Zeiss Meditec AG under the name IR800.

Optical angiography can be carried out intraoperatively without much effort and with almost no restrictions on the number of times. It supplies an image of the shallow vessels in the observation region, even in real time if required, and makes it possible to estimate blood flow changes. The perfusion cannot be quantified in absolute terms on its own, that is, without knowledge of further parameters. This means that it proves impossible to determine absolute values or absolute difference values for the flow speed and/or the volumetric flow rate, that is, the blood volume that passes through a cross section within a unit time, in (relatively large) vessels. However, the blood flow is a very important parameter in, for example, vascular—i.e. relating to blood vessels—neurosurgery.

Computed tomography angiography (CTA) uses modern multi-row computed tomography. Computed tomography is the computer-based evaluation of a multiplicity of X-ray recordings of an object, recorded from different directions, in which the non-captured volume structure is reconstructed afterward in order to produce a three-dimensional image. For diagnostic purposes, two-dimensional slice images are generated from the three-dimensional image and displayed on a monitor. It is possible to display vessels after administering a contrast agent. The functionality of a computed tomography scanner was described in GB 1283915 A for the first time.

The medical imaging method CTA not only affords the possibility of displaying the entire examined vessel structure in three dimensions, but it also makes it possible to calculate the absolute value of the volume flow, or equivalently the absolute value of the volumetric flow rate, at every point in the vessel system. After injecting a small amount of a contrast agent, which generally contains iodine, into the vascular system of the patient, the distribution of said contrast agent in the tissue is recorded using repeated scans with an overall duration of approximately 40 seconds. Here, the X-ray computed tomography scanner produces many slice images of the tissue that are successive in time with the aid of X-ray radiation. From this, a computer can calculate how long the contrast agent takes to be distributed. A method and an arrangement for a spatially resolved calculation of the absolute value of the blood flow, i.e. the flow speed and/or the volumetric flow rate of the blood through the examined vessels, are described, for example, in U.S. Pat. No. 6,373,920 B1. Information in respect of the functionality of the image evaluation is also gathered from the page http://www.innovations-report.de/html/berichte/medizin_gesundheit/bericht-25207.html.

Magnetic resonance angiography or, equally, magnetic resonance imaging (MRI) is based on very strong magnetic fields and alternating electromagnetic fields in the radiofrequency range, by means of which specific atomic nuclei are excited in the body by resonance which then induce electric signals in a detector. In order to determine the location of the respective atomic nuclei, a spatially dependent magnetic field (gradient magnetic field) is applied and thus precise three-dimensional imaging is made possible. Different relaxation times for different tissue types are an important basis for the image contrast. Additionally, the different content of hydrogen atoms in different types of tissue (for example, muscle, bone) also contributes to the image contrast. Administering a contrast agent in particular also makes it possible to display blood vessels. For assessments and for making diagnoses it is necessary for the data records, recorded as three-dimensional data records, to be displayed as two-dimensional images on the monitor. Nuclear magnetic resonance is used synonymously with magnetic resonance imaging. The abbreviation MRI, which can also be found, comes from the English words magnetic resonance imaging. A device and a method for carrying out MRI are described in, for example, U.S. Pat. No. 4,707,658.

The medical imaging method MRI also makes it possible to calculate the absolute value of the volumetric flow rate at each point in the vessel system. A method and an arrangement for quantitatively measuring the perfusion are described in, for example, United States patent application publication 2008/0119720 A1. At the address http://www.vassolinc.com/product.cfm, VasSol offers software called NOVA (Non-invasive Optimal Vessel Analysis) for quantifying the blood flow; the software uses MRA data for the calculation.

The arrangements or devices for carrying out the three-dimensional imaging methods CTA and MRI have a comparatively large design. A computed tomography scanner in the traditional C-arm design comprises two huge arms, in which an X-ray source and a CT detector lie opposite one another and circle the body of the patient. An instrument of this type is described in, for example, EP 0244596 A1. Furthermore, annular computed tomography scanners are known; here the patient is moved into the interior thereof on a couch. The X-ray source circles the patient within the ring. By way of example, an arrangement of this type is described in U.S. Pat. No. 6,373,920 B1. A magnetic resonance imaging scanner usually also has an annular design. By way of example, an arrangement of this type is shown and described in United States patent application publication 2008/0119720 A1.

As a result of the large spatial requirements, the long measurement duration and the lack or restricted accessibility to the examined tissue for the surgeon or operator and assisting medical staff during operations, such instruments or methods may generally only be used pre-operatively, or in the operating theater, only with great effort and/or intermittently with long time intervals.

Although absolute-value measuring flow probes, like, for example, an ultrasound Doppler anemometer, laser Doppler anemometer (LDA) and inductive or capacitive flow sensors, are suitable for contactless measurement of flow or particle speeds, that is, for determining the blood flow, and also supply absolute values in the case of appropriate calibration, such probes can only be used at points.

SUMMARY OF THE INVENTION

The object of the invention now includes providing an arrangement and a method for quantitatively determining the blood flow within blood vessels, which can be used intraoperatively and are possibly able to provide real-time information in respect of the current flow speed and/or the current volumetric flow rate of the blood.

The generic arrangement for quantitatively determining the blood flow within blood vessels through which blood flows in a volume of a tissue having a surface comprises a first capturing apparatus for capturing three-dimensional first image data of a first volume portion of the volume and a first calculation apparatus for spatially resolved calculation of absolute values of the flow speed and/or of the volumetric flow rate of the blood flowing through the blood vessels within the first volume portion from the three-dimensional first image data captured by the capturing apparatus. Specifically, the first capturing apparatus can be a conventional X-ray computed tomography scanner or a magnetic resonance imaging scanner, on the computer of which software has been recorded as calculation apparatus, which allows the calculation of absolute values of the flow speed and/or of the volumetric flow rate of the blood flowing through the blood vessels on the basis of the (volume) image data recorded or captured by the tomography scanner and optionally allows the output thereof on a display instrument such as, for example, a screen, a monitor or a printer. Although these absolute values can be output as numerical values on the display instrument, in general there is more likely to be a graphical representation, more particularly a false-color representation.

The invention is distinguished by the fact that in addition to the first capturing apparatus, more particularly in addition to the tomography scanner, provision is also made for a second capturing apparatus for (volume) image data, which second capturing apparatus is provided and designed for capturing second, namely optical, image data, continuously in time, of a first surface portion of the surface enclosing the volume with the blood vessels. The optical second capturing apparatus may be a video camera or comprise the latter. This video camera may be a conventional camera provided for visible light; however, it is also possible that the camera alternatively or additionally is sensitive to optical radiation in the infrared and/or ultraviolet spectral range.

It is also possible that there is not only one, but a number of video cameras. By way of example, a stereoscopic visual impression can be imparted in the case of two video cameras, in particular if the recorded images are processed accordingly for the observer.

Although the angiogram of this optical angiography or the optical image data on which this angiogram is based does not make it possible to make statements in respect of absolute values for the flow speed and/or the volumetric flow rate of the blood in the recorded or captured vessels, it is possible to make statements in respect of relative values. Thus, for example, it is possible to determine at what point the flow speed and/or the volumetric flow rate is twice as big as at another point within the captured vessel region. Furthermore, a pre/post comparison for example makes it possible to determine the relative change in the flow speed and/or in the volumetric flow rate, for example, after a surgical intervention, compared to the preoperative state. In order to determine such relative values, provision is made for a second calculation apparatus. In other words, according to the invention, provision is made for a second calculation apparatus for spatially resolved calculation of relative values of the flow speed and/or of the volumetric flow rate of the blood flowing through the blood vessels arranged directly below the first surface portion from the optical second image data captured by the optical second capturing apparatus. Specifically, provision can be made for a computer to which the video data is supplied and on which software or a computer program is installed for calculating the relative values of the flow speed and/or of the volumetric flow rate of the blood in the vessels from the captured optical second image data.

The idea of the invention now consists of using the absolute values of the flow speed and/or of the volumetric flow rate of the blood in the vessels, obtained from the first angiography, more particularly from the CT angiography or from the MR angiography, to derive absolute values of the flow speed and/or of the volumetric flow rate of the blood in the vessels from the relative values of the flow speed and/or of the volumetric flow rate of the blood in the vessels obtained from the optical angiography, that is, to calibrate the relative values with the aid of the absolute values.

However, a precondition is that there was a correct spatial assignment of the relative and absolute values required for the calibration. By way of example, it would be possible to localize at least one point for which there is both an absolute value from the three-dimensional first angiography and a relative value from the optical second angiography. Since the remaining relative values emerge from, for example, multiplying the ratio of the respective remaining relative values and the relative value at the point of the known absolute value by the known absolute value, all relative values extracted from the optical second angiography can be converted into absolute values. However, since a calibration by absolute and relative values at one point will be very inaccurate, it is more likely that during calibration there will be an averaging over a plurality of absolute and/or relative values at different points. Moreover, it may be that the points from the 3D angiography, for which the absolute values of the perfusion are available, are not identical to the points from the optical angiography, for which the relative values of the perfusion are available. Here too, it is more likely that during calibration there will be an averaging of the absolute and/or relative values at a plurality of mutually different points.

According to this, an essential component of the invention is an assignment or allocating apparatus for spatially assigning first and second image data to one another, for example based on anatomical structures and/or in the case of examination via neuronavigation. The assignment based on anatomical structures is very precise and can be carried out in real time, leading to precise and current data material. More particularly, if anatomical structures are used, or if combined with neuronavigation, it is even possible to capture a so-called "brain shift".

Furthermore, a calibration apparatus is provided in order to calibrate the relative values of the flow speed and/or of the volumetric flow rate of the blood flowing through the blood vessels arranged directly below the first surface portion on the basis of the absolute values of the flow speed and/or of the volumetric flow rate of the blood flowing through the blood vessels within the first volume portion with the first and second image data, spatially assigned to one another, for a first point in time.

Provision is now made for a third calculation apparatus in order to calculate absolute values of the flow speed and/or of the volumetric flow rate, continuously in time, of the blood flowing through the blood vessels arranged directly below the first surface portion on the basis of the calibrated relative values from the optical second image data, captured continuously in time, by the optical second capturing apparatus. This third calculation apparatus may be software, which is, for example, installed on the computer associated with the video camera. In principle, it would also be possible that this is a computer program that is installed for execution on the above-described computer associated with the first capturing apparatus, that is, in particular the computed tomography scanner. It is understood that one, more, or all calculation apparatuses may be stored on a central server in the form of computer programs, which server will be spatially deposited in the vicinity of the capturing apparatuses or, via a data transfer apparatus, at a location far away.

Finally, provision is made, according to the invention, for an output apparatus for outputting the absolute values of the flow speed and/or the volumetric flow speed of the blood flowing through the blood vessels arranged directly below the first surface portion, calculated from the optical second image data, continuously in time. The output apparatus can be a monitor or a printer. The absolute values can be output as spatially assigned numerical values, or else in the form of a graphical false-color display or the like.

A method according to the invention, more particularly an operating method for a computer or the like, for quantitatively determining the blood flow within blood vessels, through which blood flows, in a volume of a tissue with a surface, which may, for example, be carried out with the aid of the above-described arrangement, comprises the following method steps:

capturing three-dimensional first image data of a first volume portion of the volume;

spatially resolved calculation of absolute values of the flow speed and/or of the volumetric flow rate of the blood flowing through the blood vessels within the first volume portion from the captured three-dimensional first image data;

capturing optical second image data of a first surface portion of the surface;

spatially resolved calculation of relative values of the flow speed and/or of the volumetric flow rate of the blood flowing through the blood vessels arranged directly below the first surface portion from the captured optical second image data;

spatially associating corresponding three-dimensional first and optical second image data;

calibrating the relative values of the flow speed and/or of the volumetric flow rate, calculated from the captured optical second image data, of the blood flowing through the blood vessels arranged directly below the first surface portion on the basis of the absolute value of the flow speed and/or of the volumetric flow rate of the blood flowing through the blood vessels within the first volume portion using the spatially associated three-dimensional first and optical second image data for a first point in time;

calculating absolute values of the flow speed and/or of the volumetric flow rate, continuously in time, of the blood flowing through the blood vessels arranged directly below the first surface portion from the optical second image data, captured continuously in time by the second capturing apparatus, using the calibrated relative values; and, outputting the absolute values of the flow speed and/or of the volumetric flow rate, calculated continuously in time from the optical second image data, of the blood flowing through the blood vessels arranged directly below the first surface portion.

It may be desirable or even necessary, particularly when carrying out surgery on the tissue captured by optical/angiography means, to carry out a new calibration because the temperature and/or the concentration of the contrast agent and/or other parameters that change, more particularly adversely affect, the image capture may change or may have changed. If there is a change in the type or quality of the image data, there may be or may already have been a change in establishing the relative values with respect to the original state. So that it is not necessary to fall back on a recalibration with the aid of the 3D image data or even newly captured 3D image in this case, the invention provides for a flow speed and/or particle speed measuring apparatus for locally measuring absolute values of the flow speed of the blood and/or for locally measuring absolute values of the speed of particles contained in the blood. The assignment apparatus can then furthermore be designed to assign the point where the absolute values of the flow speed and/or the absolute values of the particle speed are measured to those optical second image data of the corresponding point. Finally, the calibration apparatus can furthermore be embodied to calibrate, for a second point in time, the relative values of the flow speed and/or of the volumetric flow rate of the blood flowing through the blood vessels arranged directly below the first surface portion on the basis of the absolute values of the flow speed and/or particle speed, measured by the flow speed and/or particle speed measuring apparatus, for the absolute values of the flow speed and/or the absolute values of the particle speed, associated with the points corresponding to the optical second image data.

Accordingly, the method according to the invention can also comprise the following method steps:

locally measuring an absolute value of the flow speed of the blood and/or of the speed of particles contained in the blood;

spatially assigning the measurement of the absolute value of the flow speed and/or of the particle speed to the optical second image data; and, calibrating the relative value of the flow speed and/or of the volumetric flow rate of the blood flowing through the blood vessels arranged directly below the first surface portion based on the locally measured absolute value of the flow speed and/or of the particle speed for a second point in time.

Accordingly, the calibration can be repeated, for example, with the aid of the three-dimensional first image data and/or on the basis of the locally measured absolute value of the flow speed and/or of the particle speed while capturing the optical second image data or intermittently for capturing the optical second image data.

The flow speed and/or particle speed measuring apparatus can be an ultrasound Doppler anemometer or a laser Doppler anemometer or an inductive flow sensor or a capacitive flow sensor, or the flow speed and/or particle speed measuring apparatus can comprise an ultrasound Doppler anemometer or a laser Doppler anemometer or an inductive flow sensor or a capacitive flow sensor. All these apparatuses are comparatively simple to operate and are distinguished by comparatively low spatial requirements.

In many cases, it is expedient to find the regions of the tissue to be examined quickly. By way of example, if a 3D angiography (for example CTA or MRA) is initially carried out in order to establish absolute values for the perfusion, it is important that the optical angiography is also carried out in the surface region for which 3D perfusion values are available. Conversely, if an optical angiography is carried out initially, it is important that the surface region examined with this optical angiography is found again in the 3D angiography as well. In the first case, the arrangement according to the invention can comprise an alignment apparatus for the second capturing apparatus, which alignment apparatus is designed and installed to align the optical second capturing apparatus for allowing capture of the optical second image data of the first surface portion of the surface, continuously in time, on the basis of the three-dimensional first image data captured by the first capturing apparatus. In the second case, the arrangement can comprise an alignment apparatus for the first capturing apparatus, which alignment apparatus is designed and installed to align the first capturing apparatus for allowing capture of the three-dimensional first image data of the first volume portion of the volume on the basis of the optical second image data captured by the second capturing apparatus.

BRIEF DESCRIPTION OF THE DRAWINGS

The invention will now be described with reference to the drawings wherein:

FIG. 3 shows a first exemplary embodiment of a method according to the invention for quantitatively determining the blood flow within blood vessels;

FIG. 4 shows a second exemplary embodiment of a method according to the invention for quantitatively determining the blood flow within blood vessels; and, FIG. 5 shows a third exemplary embodiment of a method according to the invention for quantitatively determining the blood flow within blood vessels.

DESCRIPTION OF THE PREFERRED
EMBODIMENTS OF THE INVENTION

Figure 1:
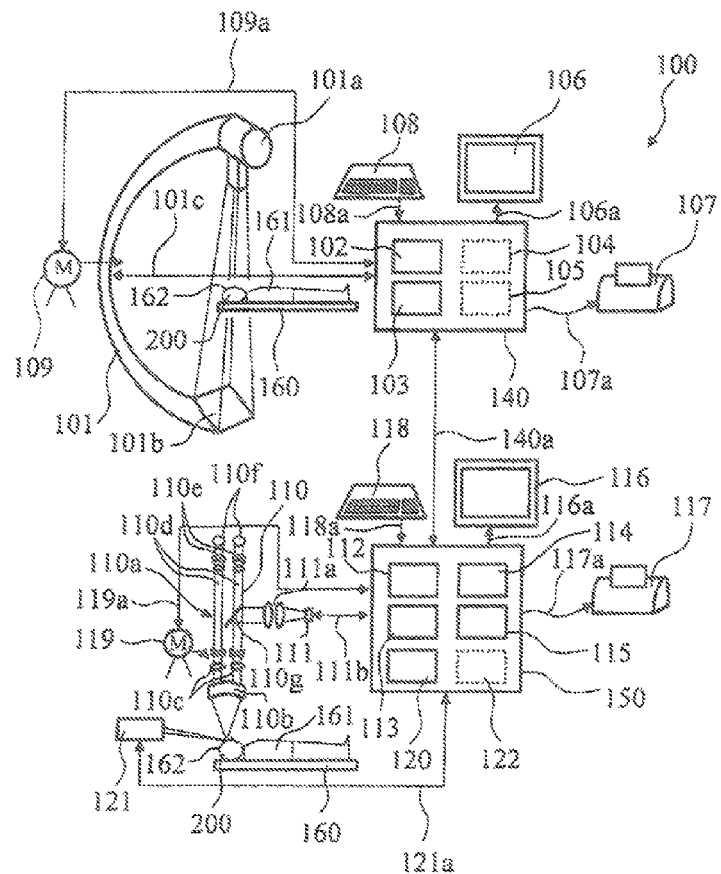
FIG. 1 shows a first exemplary embodiment of an arrangement according to the invention for quantitatively determining the blood flow within blood vessels.

FIG. 1 shows a first exemplary embodiment of an arrangement 100 according to the invention for quantitatively determining the blood flow within blood vessels. The arrangement 100 comprises an X-ray computed tomography scanner 101 in the form of a C-arm, and a surgical microscope 110 with a video camera 111 coupled thereto.

Figure 2:
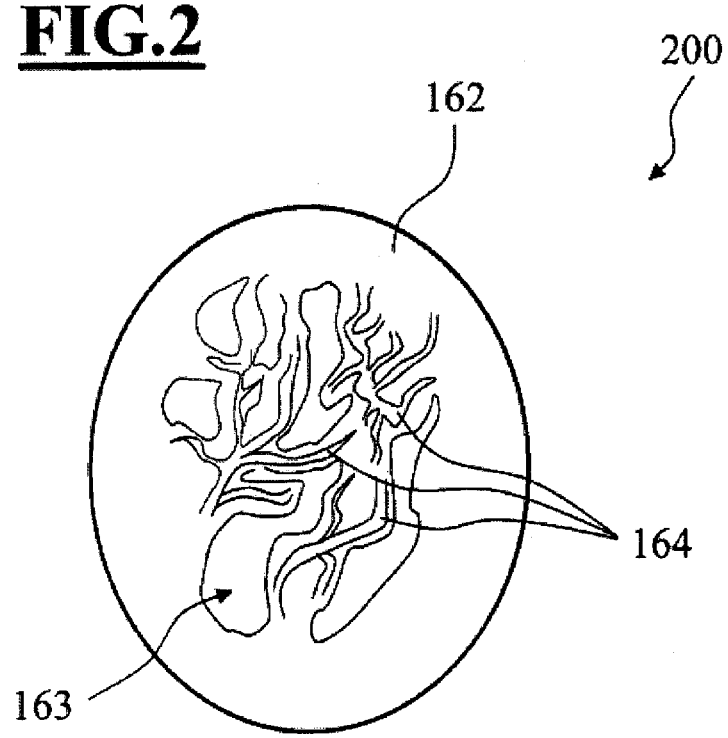
FIG. 2 shows blood vessels through which blood flows in a volume of a tissue with a surface, which tissue is examined using the arrangement according to the invention according to FIG. 1.

The C-arm 101 is embodied in the usual fashion per se. It comprises two huge arms, at the outer ends of which an X-ray source 101a and an X-ray detector 101b lie diametrically opposite to one another. The two arms with the X-ray source 101a and the X-ray detector 101b can circle around the body, more particularly, for example, the head 200, of a patient 161 lying on a couch 160. In the present case, X-ray source 101a and X-ray detector 101b are arranged lying opposite one another such that the X-ray beams, directed at the X-ray detector 101b, of the X-ray source 101a pass through the head 200 of the patient 161 and allow a CT angiographic recording of the tissue 163 of the brain 162 with the blood vessels 164, as illustrated in, for example, FIG. 2.

The X-ray computer tomography scanner 101 is connected to a computer 140 via a data line 101c. This computer 140 is firstly designed for controlling the functionality of the computed tomography scanner 101 and secondly allows the data capture and evaluation of three-dimensional image data of the type described in the introduction of the description. More particularly, it comprises a calculation module 102 with a computer program having program code allowing the spatially resolved calculation of absolute values of the flow speed and/or of the volumetric flow rate of the blood flowing through the blood vessels within the examined tissue 163 from the three-dimensional image data captured by the computed tomography scanner 101. In the present exemplary embodiment, these absolute values can be displayed in the form of a false-color representation on the monitor 106 together with the vessel structures 164 captured by the computed tomography scanner 101, which monitor is connected to the computer 140 via a data line 106a. Optionally, a representation is also possible by means of the printer 107, which is likewise connected to the computer 140 via a data line 107a.

Furthermore, provision is made for a keyboard 108, which is connected to the computer 140 via a data line 108a in order to offer a user the option of setting various functionalities of the computed tomography scanner 101 or other connected instruments.

Finally, the computer 140 is also connected to one or more servomotors 109 via a control line 109a, which servomotors make it possible to move the C-arm 101 into any position with respect to the body of the patient 161. To this end, the computer 140 comprises a calculation module 103 with a computer program having program code. On the one hand, the servomotor-control calculation module 103 is designed and installed to actuate the servomotors 109 when the user requests this via the keyboard 108; on the other hand provision is made for setting the position of the C-arm 101 in accordance with a predetermined scanning programs (in this respect cf. the reference in the introduction of the description) or else on the basis of information obtained via the data line 140a, as will be described in detail below.

The computer 140 will in general comprise additional calculation modules (104, 105) in the form of computer programs having program code, which programs are required or expedient for the functionality of the system. The corresponding calculation modules (104, 105) are illustrated in a dashed fashion in the drawing.

The surgical microscope 110 is embodied in a fashion known per se. It comprises a microscope optical system 110a with a main objective 110b having an optical axis (not illustrated here) that passes through the center of the main objective 110b. The object to be examined, in this case the brain 162 of the patient 161 lying on the couch 160, is arranged in the object plane of the main objective 110b. Optical radiation (for example, visible, infrared and/or ultraviolet light) emerging from the brain 162 is converted into a parallel bundle of rays by the main objective 110b. In the parallel bundle of rays, two zoom systems 110c are arranged at a distance from the optical axis. These zoom systems respectively take a partial bundle of rays 110d from the parallel bundle of rays and route them to eyepieces 110e via deflection prisms (not shown in the figure of the drawing), into which eyepieces an observer looks with his left and right eye 110f in order to perceive an enlarged representation of the object, namely the brain 162, as an image. Here, the image perceived by the left eye corresponds to an image when viewed under an angle ($\alpha$) to the optical axis and the image perceived by the right eye corresponds to an image when viewing the object under an angle $-\alpha$ to the optical axis such that the observer overall obtains a stereoscopic image of the object 162 when using both eyes 110f.

A partly transparent mirror 110g is arranged in one of the partial bundles of rays 110d in order to decouple part of the optical radiation as a beam. The beam is transmitted via a camera adapter optical system 111a onto a light-sensitive area of the video camera 111 such that it records an image of the object 162 as observed at an angle $-\alpha$ to the optical axis. The images recorded by the camera 111 are transmitted to a computer 150 via a data line 111b as image data. In the present case, the light-sensitive area of the camera 111 is sensitive to infrared light. Accordingly, the camera 111 allows the emission of the fluorescent dye indocyanine green (ICG) to be detected, which fluorescent dye is enriched in the blood of the patient 161 after a corresponding bolus was administered and firstly ensures the visibility of the vessel structure 164 of the examined tissue 163 and secondly, as progressing dye front, allows the capture of the movement of the blood flowing through the vessels 164.

The computer 150 comprises a plurality of calculation modules (112, 113, 114, 115, 120, 122) in the form of computer programs with program code. The calculation module 112 constitutes a calculation apparatus for spatially resolved calculation of relative values of the flow speed and/or of the volumetric flow rate of the blood flowing through the blood vessels 164 arranged directly below the surface from the optical image data captured by the camera 111. The calculation module 113 is designed as assignment apparatus in order to assign, in space, the image data from the X-ray computed tomography scanner 101, which are provided to the computer 150 by the computer 140 via the data line 140a, to the optical image data captured continuously in time by the video camera 111. The language of the art often also uses the term "matching" for this procedure. In other words, there is matching of the vessels 164 observed by the video camera 111 to the images of the vessels 164 recorded with the aid of the computed tomography scanner 101. This can be brought about either by neuronavigation or by comparing characteristic anatomical structures themselves, in particular by comparing the profile or orientation of the blood vessels 164.

The computer 150 furthermore comprises the calculation module 114, referred to as calibration module 114 below. This calibration module 114 acts as calibration apparatus for calibrating the relative values of the flow speed and/or of the volumetric flow rate of the blood flowing through the blood vessels 164 arranged directly below the surface on the basis of the absolute values of the flow speed and/or of the volumetric flow rate of the blood flowing through the blood vessels 164 of the volume captured by the CT angiography carried out by the X-ray computed tomography scanner 101 with the spatially matched CT image data and video image data for a first point in time. The calculation module 115 is provided and installed to calculate absolute values of the flow speed and/or of the volumetric flow rate, continuously in time, of the blood flowing through the blood vessels arranged directly below the surface captured by the video camera 111 on the basis of the calibrated relative values from the optical image data captured, continuously in time, by the video camera 111. Thus, in the following text, this calculation module 115 is also referred to as absolute value calculator.

A monitor 116 is also connected to the computer 150 via a data line 116a. Furthermore, a printer 117 is connected to the computer 150 via the data line 117a. Both apparatuses, namely the monitor 116 and the printer 117, serve as output apparatuses for outputting the absolute values of the flow speed and/or of the volumetric flow rate of the blood flowing through the blood vessels 164 arranged directly below the surface captured by the video camera 111, calculated continuously in time from the optical image data from the video camera.

Finally, a keyboard 118 is connected to the computer 150 via a data line 118a in order to operate the surgical microscope 110, the video camera 111 and the output apparatuses 116, 117.

As a further particular functionality, the surgical microscope 110 equipped with one or more servomotors 119, which make it possible to align the surgical microscope with respect to the tissue to be examined. The servomotors 119, of which merely one is explicitly illustrated in FIG.1, are actuated via a control line 119a, is which the servomotors 119 are connected to the computer 150. The calculation module 120, also referred to as servomotor control 120 below, ensures that the surgical microscope 110 is aligned on the basis of manually entered commands, entered for example via the keyboard 118; an automatically executed, algorithm; or on the basis of information that can be provided to the computer 150 from the computer 140 via the data line 140a. In a particular embodiment of the invention, the calculation Module 120 is installed and embodied such that the surgical microscope 110 and, more particularly, the video camera 111 are aligned to enable the capture, continuously in time, of optical image date of the desired surface based on the 3-dimensional image data captured by the CT arm 101. Accordingly, the calculation. module 103 in the present exemplary embodiment is installed andembodied such that the servomotors. 109 for the C-arm 101 are aligned to enable the capture of 3-dimensional image data of the volume matched to the surface based on the optical image data captured by the video camera 111.

Like the computer 140, the computer 150 can be equipped with further functionalities. In the exemplary embodiment, this is identified with the aid of the calculation module 122, which is illustrated using a dashed line.

In addition to the two angiographic capturing apparatuses, the computed tomography scanner 101 and the video camera 111, the arrangement 100 comprises an inductive flow sensor 121. This inductive flow sensor 121 is connected to the computer 150 via a data line 121a. The inductive flow sensor 121 is suitable for locally measuring absolute values of the flow speed of the blood flowing through the examined tissue 163.

The matching module 113 is furthermore designed to match spatially the point of measuring the absolute values of the flow speed to the optical image data captured by the video camera 111.

The calibration module 114 is designed to calibrate, for a second point in time, the relative values of the flow speed of the blood flowing through the blood vessels 164 arranged directly below the surface captured by the video camera 111 on the basis of the absolute values of the flow speed, measured by the inductive flow sensor 121, for absolute values of the flow speed matched to the spatially matched optical image data from the video camera 111.

For the sake of completeness, reference is made to the fact that any other flow speed and/or particle speed sensor, such as, for example, an ultrasound Doppler anemometer or a laser Doppler anemometer or a capacitive flow sensor, can be used instead of the inductive flow sensor 121.

The method according to the invention will be explained below based on three exemplary embodiments. FIGS. 3 to 5 specify the individual method steps of the three methods, described in an exemplary fashion, in the form of flowcharts (300, 400, 500). In principle, all three methods can be carried out fully automatically, that is, in particular with the aid of a computer, on which a corresponding computer program has been stored.

The first exemplary embodiment of a method according to the invention, illustrated in FIG. 3, for quantitatively determining the blood flow within blood vessels is in principle based on combining a quantitatively measuring preoperative angiography, such as, for example, a CTA or an MR angiography, with an optical angiography, which can be used intraoperatively and with the aid of which relative values for the perfusion of examined blood vessels can be determined.

After starting the method in a first start step 301, a preoperative angiography is first of all recorded (method step 302). By way of example, this can be carried out using the C-arm 101 sketched in FIG. 1 or, alternatively, with the aid of a magnetic resonance imaging scanner. To this end, the patient is positioned on a couch and the body region to be examined is scanned by the computed tomography scanner.

In a next step 303, there is quantitative evaluation of the blood flow volumes in the vessels captured or registered with the aid of the preoperative angiography. Quantitative evaluation of the blood flow volumes should be understood to mean the spatially resolved calculation of absolute values of the flow speed or the spatially resolved calculation of absolute values of the volumetric flow rate of the blood flowing through the examined blood vessels.

The patient is then removed from the scanning space of the computed tomography scanner and, if need be, moved into the operating theater. Then, for example, a surgical microscope with IR800 functionality is directed on the body region to be examined and surgery is prepared by medical staff. In a further step 304, an optical angiography is carried out intraoperatively. The exemplary embodiment according to FIG. 3 is a fluorescence angiography. Administering a bolus of a fluorescent dye, preferably indocyanine green (ICG), by injection into the blood vessels of the patient makes it possible to capture, in high contrast, the blood vessels to be examined of the patient with the aid of an infrared-sensitive video camera.

In a further method step 305, there is a semiquantitative evaluation of the blood flow volumes, that is, relative values for the flow speed and/or the volumetric flow rate of the blood flowing through the blood vessels are calculated in the vessels registered intraoperatively.

In the subsequent step 306, there is an association between the blood vessels observed with the IR800 angiography and the images recorded preoperatively with the aid of CTA, that is, there is so-called "matching".

In a further step 307, the preoperative blood flow volumes are matched to the vessels registered intraoperatively and, subsequently in step 308, there is the calibration of the intraoperative semiquantitative blood flow volumes with respect to the preoperative blood flow volumes.

All subsequent intraoperative IR800 measurements are quantified in absolute terms based on this calibration. In the flowchart 300 according to FIG. 3, this absolute quantification is expressed by repeated application of method steps 309 to 312: thus, first of all, there is another intraoperative IR800 angiography (method step 309). Thereafter, there is a semiquantitative evaluation of the blood flow volumes in the vessels registered intraoperatively (method step 310) and, subsequently, there is an absolute quantification of the blood flow volumes in the vessels registered intraoperatively on the basis of the calibration according to method step 308. Finally, there is an output on a monitor or a printer of the blood flow volumes, quantified in absolute terms, in the vessels registered intraoperatively (method step 312). To the extent that a further analysis should be continued (query 313), method steps 309 to 312 are repeated until the user terminates the method (method step 314).

The second exemplary embodiment of a method according to the invention, illustrated in FIG. 4, for quantitatively determining the blood flow within blood vessels in principle is based, like the method according to FIG. 3, on combining a quantitatively measuring angiography with an optical angiography. However, deviating from the method illustrated in FIG. 3, provision is made for intermittently carrying out a recalibration. After starting the method in a first start step 401, a preoperative angiography is first of all recorded in a method step 402. In a next step 403, there is a quantitative evaluation of the blood flow volumes in the vessels captured or registered with the aid of the preoperative angiography. In a further step 404, an optical angiography is carried out intraoperatively. In a further method step 405, there subsequently is a semiquantitative evaluation of the blood flow volumes, that is, relative values for the flow speed and/or the volumetric flow rate of the blood flowing through the blood vessels are calculated in the vessels registered intraoperatively. In the following step 406, there is matching between the blood vessels observed using the IR800 angiography and the three-dimensional images recorded preoperatively. In a further step 407, the preoperative blood flow volumes are matched to the vessels registered intraoperatively and, subsequently in step 408, there is the calibration of the intraoperative semiquantitative blood flow volumes with respect to the preoperative blood flow volumes. Another intraoperative IR800 angiography is carried out in method step 409. Method step 410 then provides for a semiquantitative evaluation of the blood flow volumes in the vessels registered intraoperatively. There subsequently is an absolute quantification of the blood flow volumes in the vessels registered intraoperatively based on the calibration according to method step 408. Finally, there is an output on a monitor or a printer of the blood flow volumes, quantified in absolute terms, in the vessels registered intraoperatively (method step 412). To the extent that a further analysis should be continued (query 413), there is a query 414 as to whether a recalibration should be carried out. If this query 414 is answered in the negative, method steps 409 to 412 are repeated and if it is answered in the positive, method steps 402 to 412 are carried out; this is continued until the user terminates the method (method steps 413, 415).

The third exemplary embodiment of a method according to the invention, sketched out in FIG. 5 in the form of a flowchart, for quantitatively determining the blood flow within blood vessels in principle is based, like the method according to FIG. 4, on combining a quantitatively measuring angiography with an optical angiography and, intermittently, has the option of a recalibration. Instead of the recalibration based on a 3D angiography, the method according to FIG. 5 provides the option of recalibrating with the aid of a point measurement by a flow sensor.

After starting the method in a first start step 501, a preoperative 3D angiography is recorded in method step 502. In a next step 503, there is a quantitative evaluation of the blood flow volumes in the vessels captured or registered with the aid of the preoperative angiography. In a step 504, an optical angiography is carried out intraoperatively. In a method step 505, there then is a semiquantitative evaluation of the blood flow volumes, that is, relative values for the flow speed and/or the volumetric flow rate of the blood flowing through the blood vessels are calculated in the vessels registered intraoperatively. In the following step 506, there is matching between the blood vessels observed using the optical angiography and the three-dimensional images recorded preoperatively. In a step 507, the preoperative blood flow volumes are matched to the vessels registered intraoperatively and, in step 508, there is the calibration of the intraoperatively determined semiquantitative blood flow volumes with respect to the preoperative blood flow volumes. Another intraoperative optical angiography is carried out in method step 509. Method step 510 then provides for a semiquantitative evaluation of the blood flow volumes in the vessels registered intraoperatively. There subsequently is an absolute quantification of the blood flow volumes in the vessels registered intraoperatively based on the calibration according to method step 508. Finally, there is an output on a monitor or a printer of the blood flow volumes, quantified in absolute terms, in the vessels registered intraoperatively (method step 512). To the extent that, as determined in query 513, a further analysis should be carried out, there is a query 514 as to whether a recalibration is desired. If this query 514 is answered in the negative, method steps 509 to 512 are repeated. If the query 514 is answered in the positive, method steps 515 to 520 are first of all carried out, and then followed by method steps 509 to 512, until the user terminates the method (method steps 513, 521).

The recalibration is performed using the following method steps: first of all, there is a point measurement of the blood flow volume in a vessel with the aid of the aforementioned flow sensor (step 515). In general, this measurement can be carried out intraoperatively. That is to say, the patient need not be removed from the operating region and no instruments that hinder the surgery being carried out need to circle around the tissue to be examined.

Then an IR800 angiography is performed, likewise intraoperatively, in step 516 and, in step 517, there is a semiquantitative evaluation of the blood flow volumes in the data obtained intraoperatively with the aid of the IR800 function. In step 518, the point of the point measurement of the flow speed from step 515 is matched to a point in the vessels observed with the aid of the IR800 angiography. Thereafter, in step 519, the blood flow volumes measured at points are matched to the vessels registered intraoperatively and finally, in step 520, there is a calibration of the corresponding semiquantitative blood flow volume to the blood flow volume measured at points with the flow sensor It is understood that the foregoing description is that of the preferred embodiments of the invention and that various changes and modifications may be made thereto without departing from the spirit and scope of the invention as defined in the appended claims.

LIST OF REFERENCE SIGNS

100 Arrangement for quantitatively determining the blood flow
101 X-ray computed tomography scanner in the form of a C-arm
101a X-ray source
101b X-ray detector
101c Data line
102 Calculation module comprising a computer program having program code (absolute value computer)
103 Calculation module comprising a computer program having program code (servomotor control)
104 Calculation module comprising a computer program having program code
105 Calculation module comprising a computer program having program code
106 Monitor
106a Data line
107 Printer
107a Data line
108 Keyboard
108a Data line
109 Servomotor(s)
109a Control line
110 Surgical microscope
110a Microscope optical system
110b Main objective
110c Zoom systems
110d Partial bundle of rays
110e Eyepieces
110f Eyes
110g Partly transparent mirror
111 Camera
111a Camera adapter optical system
111b Data line
112 Calculation module comprising a computer program having program code (relative value computer)
113 Calculation module comprising a computer program having program code (matching module)
114 Calculation module comprising a computer program having program code (calibration module)
115 Calculation module comprising a computer program having program code (absolute value computer)
116 Monitor
116a Data line
117 Printer
117a Data line
118 Keyboard
118a Data line
119 Servomotor(s)
119a Control line
120 Calculation module comprising a computer program having program code (servomotor control)
121 Inductive flow sensor
121a Data line
122 Calculation module comprising a computer program having program code
140 Computer
140a Data line
150 Computer
160 Couch
161 Patient
162 Brain
163 Tissue
164 Blood vessels
200 Head
300 Flowchart
301 Surgical step
312 Surgical step
313 Decision step
314 Surgical step
401 Surgical step
413 Decision step
414 Decision step
415 Surgical step
501 Surgical step
512 Surgical step 513 Decision step
514 Decision step
515 Surgical step
521 Surgical step

What is claimed is:

1. A device for quantitatively determining the blood flow within blood vessels through which blood flows in a volume of a tissue defining a surface, the device comprising:
 a first detecting unit for capturing three-dimensional first image data of a first volume portion of said volume;
 a first calculating unit for the spatially-resolved calculation of absolute values of a flow speed and/or of a volumetric flow of the blood flowing through the blood vessels within said first volume portion from said three-dimensional first image data;
 an optical second detecting unit for capturing optical second image data continuously in time of a first surface portion of said surface;
 a second calculating unit for the spatially-resolved calculation of relative values of the flow speed and/or of the volumetric flow of the blood flowing through the blood vessels disposed directly below said first surface portion from said optical second image data;
 an allocation unit for spatially allocating said first and second image data;
 a calibrating unit for calibrating the relative value of said flow speed and/or the volumetric flow of the blood flowing through the blood vessels disposed directly below said first surface portion based on said absolute values of the flow speed and/or of said volumetric flow of the blood, which flows through said blood vessels within said first volume portion, with said first and second image data for a first time point, said first and second image data being spatially allocated with respect to each other;
 a third calculating unit for calculating absolute values of the flow speed and/or of the volumetric flow, continuously in time, of the blood flowing through the blood vessels arranged directly below said first surface portion on the basis of the calibrated relative values from the optical second image data, captured continuously in time, by said optical second detecting unit; and,
 an output unit for outputting the absolute values of the flow speed and/or the volumetric flow of the blood flowing through the blood vessels arranged within said first volume portion, calculated from said optical second image data, continuously in time.

2. The device of claim 1, wherein said first detecting unit is an x-ray computer tomography scanner or a magnetic resonance tomography scanner.

3. The device of claim 2, wherein said optical second detecting unit includes a video camera.

4. The device of claim 1, further comprising:
 a flow speed measuring unit for making local measurements of absolute values of the flow speed of the blood, local measurements of absolute values of a particle speed of particles contained in the blood or local measurements of absolute values of the flow speed and local measurements of absolute values of the particles speed;
 said allocation unit being further configured to allocate the location of the measurement of the absolute values of the flow speed, the absolute values of the particle speed or the absolute values of the flow speed and the absolute values of the particles speed of those optical second image data of the location of the measurement of the absolute values; and,
 said calibrating unit being further configured to calibrate the relative values of said flow speed, the volumetric flow or said flow speed and volumetric flow of the blood flowing through the blood vessels disposed directly below said first surface portion based on absolute values of the flow speed, particle speed or the flow speed and the particle speed for the absolute values of the flow speed, absolute values of the particle speed or the absolute values of the flow speed and the particle speed for a second time point, said absolute values of the flow speed, particle speed or flow speed and particle speed being measured by said flow speed measuring unit and said absolute values of the flow speed being allocated to said optical second image data.

5. The device of claim 4, wherein said flow speed measuring unit includes an ultrasound Doppler anemometer or a laser-Doppler anemometer or an inductive flow sensor or a capacitive flow sensor.

6. The device of claim 5, further comprising an alignment unit for said second detecting unit which alignment unit is configured to align said optical second detecting unit for allowing capture of said optical second image data of said first surface portion of said surface, continuously in time, on the basis of the three-dimensional first image data captured by said first detecting unit.

7. The device of claim 5, further comprising an alignment unit for said first detecting unit which alignment unit is configured to align said first detecting unit for allowing detection of the three-dimensional first image data of the first volume portion of the volume on the basis of the optical second image data detected by said second detecting unit.

8. A method for quantitatively determining the blood flow within blood vessels, through which blood flows, in a volume of a tissue defining a surface, the method comprising the steps of:
 capturing three-dimensional first image data of a first volume portion of the volume;
 performing a spatially resolved calculation of absolute values of the flow speed and/or of the volumetric flow of the blood flowing through the blood vessels within the first volume portion from the captured three-dimensional first image data;
 capturing optical second image data of a first surface portion of the surface;
 performing a spatially resolved calculation of relative values of the flow speed and/or of the volumetric flow of the blood flowing through the blood vessels arranged directly below the first surface portion from the captured optical second image data;
 spatially associating corresponding three-dimensional first and optical second image data;
 calibrating the relative values of the flow speed and/or of the volumetric flow, calculated from the captured optical second image data, of the blood flowing through the blood vessels arranged directly below the first surface portion on the basis of the absolute value of the flow speed and/or of the volumetric flow of the blood flowing through the blood vessels within the first volume portion using the spatially associated three-dimensional first and optical second image data for a first point in time;
 calculating absolute values of the flow speed and/or of the volumetric flow, continuously in time, of the blood flowing through the blood vessels arranged directly below the first surface portion from the optical second image data, captured continuously in time by the second capturing apparatus, using the calibrated relative values; and, outputting the absolute values of the flow speed and/or of the volumetric flow, calculated continuously in time from the optical second image data, of the blood flowing through the blood vessels arranged within said first volume portion.

9. The method of claim 8, wherein said three-dimensional first image data are determined with the aid of an x-ray computer tomography scanner or a magnetic resonance tomography scanner.

10. The method of claim 8, wherein said second optical image data are video image data.

11. The method of claim 8, wherein the allocation of said three-dimensional first image data and the optical second image data is carried out via neuronavigation, by a comparison of anatomical structures or via neuronavigation and by a comparison of anatomical structures.

12. The method of claim 8, comprising the further steps of:
locally measuring an absolute value of the flow speed of the blood, of the particle speed contained in the blood or of the flow speed of the blood and the particle speed;
spatially assigning the measurement of the absolute value of the flow speed, of the particle speed or of the flow speed and the particle speed to the optical second image data; and,
calibrating the relative value of the flow speed, of the volumetric flow or of the flow speed and the volumetric flow of the blood at the corresponding location, said blood flowing through the blood vessels arranged directly below the first surface portion, based on the locally measured absolute value of the flow speed, of the particle speed or of the flow speed and of the particle speed for a second point in time.

13. The method of claim 8, wherein the calibration can be repeated with the aid of the three-dimensional first image data; on the basis of the locally measured absolute value of the flow speed, of the particle speed or of the flow speed and the particle speed; or with the aid of the three-dimensional first image data, on the basis of the locally measured absolute value of the flow speed, of the particle speed or the flow speed and the particle speed while capturing the optical second image data or intermittently for capturing the optical second image data.

14. A non-transitory computer program stored on a computer readable medium having a program code for carrying out the method of claim 8 when said program is carried out in a computer.

15. A computer which is configured to carry out the method of claim 8.

* * * * *

UNITED STATES PATENT AND TRADEMARK OFFICE
CERTIFICATE OF CORRECTION

| | |
|---|---|
| PATENT NO. | : 8,483,796 B2 |
| APPLICATION NO. | : 13/335559 |
| DATED | : July 9, 2013 |
| INVENTOR(S) | : Werner Nahm |

Page 1 of 1

It is certified that error appears in the above-identified patent and that said Letters Patent is hereby corrected as shown below:

In the Specification in Column 10:

Line 20: insert -- is -- before "equipped".

Line 24: delete "is" and substitute -- via -- therefor.

Line 29: delete "executed, algorithm" and substitute -- executed algorithm -- therefor.

Line 32: delete "Module" and substitute -- module -- therefor.

Line 36: delete "date" and substitute -- data -- therefor.

Line 39: delete "andembodied" and substitute -- and embodied -- therefor.

Line 39: delete "servomotors." and substitute -- servomotors -- therefor.

In Column 14:

Insert -- 412 Surgical step -- between lines 62 and 63.

In the Claims in Column 15:

Line 60: delete "particles" and substitute -- particle -- therefor.

Line 65: delete "particles" and substitute -- particle -- therefor.

Signed and Sealed this
First Day of October, 2013

Teresa Stanek Rea
*Deputy Director of the United States Patent and Trademark Office*